US010410838B2

(12) United States Patent
Hanson et al.

(10) Patent No.: US 10,410,838 B2
(45) Date of Patent: Sep. 10, 2019

(54) APPARATUS AND METHOD FOR PLASMA TREATMENT OF CONTAINERS

(75) Inventors: Daniel R. Hanson, New Richmond, WI (US); Moses M. David, Woodbury, MN (US); David J. White, Amery, WI (US); Jean A. Kelly, Woodbury, MN (US); Todd D. Alband, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1039 days.

(21) Appl. No.: 13/318,962

(22) PCT Filed: May 6, 2010

(86) PCT No.: PCT/US2010/033884
§ 371 (c)(1),
(2), (4) Date: Nov. 4, 2011

(87) PCT Pub. No.: WO2010/129783
PCT Pub. Date: Nov. 11, 2010

(65) Prior Publication Data
US 2012/0045590 A1  Feb. 23, 2012

Related U.S. Application Data

(60) Provisional application No. 61/175,887, filed on May 6, 2009, provisional application No. 61/175,898, filed on
(Continued)

(51) Int. Cl.
*H01J 37/32* (2006.01)
*A61M 15/00* (2006.01)
(Continued)

(52) U.S. Cl.
CPC ..... *H01J 37/32394* (2013.01); *A61M 15/009* (2013.01); *B05D 1/62* (2013.01);
(Continued)

(58) Field of Classification Search
CPC ........... H01J 37/32394; H01J 37/32366; H01J 37/3244; H01J 37/32513; A61M 15/009;
(Continued)

(56) References Cited

U.S. PATENT DOCUMENTS 4,521,286 A   6/1985  Horwitz
4,931,135 A * 6/1990  Horiuchi et al. ............... 216/67
(Continued)

FOREIGN PATENT DOCUMENTS

DE  102005035247  *  2/2007  ........... C23C 16/455
EP       0497204         8/1992
(Continued)

OTHER PUBLICATIONS van Ooij, Plasma-polymerized coatings of trimethylsilane deposited on cold-rolled steel substrates Part 2. Effect of deposition conditions on corrosion performance:, Progress in Organic Coatings, 1995, vol. 25, pp. 319-337.
(Continued)

*Primary Examiner* — Benjamin Kendall

(57) ABSTRACT

An apparatus (9) for plasma treating multiple containers. The apparatus includes a manifold (2) comprising at least a first chamber with multiple outlet openings and multiple hollow, electrically-conductive nozzles (10) for at least one of delivering or exhausting plasma-generating gas. The multiple hollow, electrically-conductive nozzles are connected to the multiple outlet openings and protrude from the manifold. A method of plasma treating multiple containers is also disclosed. The method includes providing a reactor system comprising an apparatus disclosed herein, inserting the multiple hollow, electrically-conductive nozzles into the multiple containers (30), evacuating the multiple containers, grounding the multiple hollow, electrically-conductive nozzles while applying radio frequency power to the mul-
(Continued)

tiple containers, providing a gas inside the containers, and generating a plasma. At least one of evacuating or providing the gas is carried out through the hollow, electrically-conductive nozzles.

19 Claims, 5 Drawing Sheets

Related U.S. Application Data on May 6, 2009, provisional application No. 61/320,361, filed on Apr. 2, 2010.

(51) Int. Cl.
| | |
|---|---|
| B05D 1/00 | (2006.01) |
| B05D 3/14 | (2006.01) |
| B05D 5/08 | (2006.01) |
| B05D 7/22 | (2006.01) |
| C23C 16/04 | (2006.01) |
| C23C 16/455 | (2006.01) |

(52) U.S. Cl.
CPC .............. *B05D 3/142* (2013.01); *B05D 5/083* (2013.01); *B05D 7/227* (2013.01); *C23C 16/045* (2013.01); *C23C 16/45578* (2013.01); *H01J 37/3244* (2013.01); *H01J 37/32366* (2013.01); *A61M 2205/0238* (2013.01); *B05D 2202/25* (2013.01)

(58) Field of Classification Search
CPC . A61M 2205/0238; B05D 1/62; B05D 3/142; B05D 5/083; B05D 7/227; B05D 2202/25; C23C 16/045; C23C 16/45578
See application file for complete search history.

(56) References Cited

U.S. PATENT DOCUMENTS

| | | | |
|---|---|---|---|
| 4,980,196 A | 12/1990 | Yasuda | |
| 4,991,822 A | 2/1991 | Enke | |
| 5,133,986 A | 7/1992 | Blum | |
| 6,015,597 A | 1/2000 | David | |
| 6,197,120 B1 | 3/2001 | David | |
| 6,276,296 B1* | 8/2001 | Plester | C23C 16/045 |
| | | | 118/723 E |
| 6,424,091 B1* | 7/2002 | Sawada et al. | 315/111.81 |
| 6,540,839 B1 | 4/2003 | Lee | |
| 6,649,222 B1 | 11/2003 | D'Agostino | |
| 6,696,157 B1 | 2/2004 | David | |
| 6,758,910 B2* | 7/2004 | Schmoyer | C08J 7/14 |
| | | | 118/715 |
| 6,806,651 B1 | 10/2004 | Chistyakov | |
| 6,878,419 B2 | 4/2005 | David | |
| 7,481,886 B2* | 1/2009 | Kato | C23C 16/455 |
| | | | 118/715 |
| 8,104,469 B2 | 1/2012 | Dams | |
| 8,414,956 B2 | 4/2013 | Jinks | |
| 8,430,097 B2 | 4/2013 | Jinks | |
| 8,616,201 B2 | 12/2013 | Jinks | |
| 8,808,786 B2 | 8/2014 | Jinks | |
| 8,815,325 B2 | 8/2014 | David | |
| 2002/0142105 A1 | 10/2002 | Hum | |
| 2002/0182319 A1* | 12/2002 | Ben-Malek et al. | 427/237 |
| 2003/0232150 A1* | 12/2003 | Arnold | B08B 9/426 |
| | | | 427/569 |
| 2004/0099214 A1* | 5/2004 | Hama et al. | 118/723 E |
| 2005/0133025 A1 | 6/2005 | Laiho | |
| 2005/0227019 A1* | 10/2005 | Hama et al. | 427/581 |
| 2008/0017113 A1* | 1/2008 | Goto et al. | 118/723 R |
| 2009/0042321 A1* | 2/2009 | Sasaki | H01J 37/32449 |
| | | | 438/10 |
| 2009/0081382 A1* | 3/2009 | Kraus et al. | 427/569 |
| 2009/0280268 A1* | 11/2009 | Glukhoy | C23C 16/045 |
| | | | 427/578 |
| 2011/0308458 A1* | 12/2011 | Sung | C23C 16/45565 |
| | | | 118/719 |
| 2012/0097159 A1 | 4/2012 | Iyer | |

FOREIGN PATENT DOCUMENTS

| | | |
|---|---|---|
| EP | 0 642 992 | 3/1995 |
| EP | 1010773 | 6/2000 |
| KR | 100829925 | 5/2008 |
| WO | 1996-32099 | 10/1996 |
| WO | 1996-32150 | 10/1996 |
| WO | 1996-32151 | 10/1996 |
| WO | 1996-32345 | 10/1996 |
| WO | 1997-41729 | 11/1997 |
| WO | 1999-42154 | 2/1999 |
| WO | 2001-64273 | 9/2001 |
| WO | 2001-64274 | 9/2001 |
| WO | 2001-64275 | 9/2001 |
| WO | 2001-64524 | 9/2001 |
| WO | 2002-30498 | 4/2002 |
| WO | 2002-47829 | 6/2002 |
| WO | 2003-006181 | 1/2003 |
| WO | 2003-024623 | 3/2003 |
| WO | 2003-035154 | 5/2003 |
| WO | 2003-095009 | 11/2003 |
| WO | 2007-007995 | 1/2007 |
| WO | 2008-146022 | 12/2008 |
| WO | 2008-146024 | 12/2008 |
| WO | 2008-146025 | 12/2008 |
| WO | 2009-036579 | 3/2009 |
| WO | 2009-061891 | 5/2009 |
| WO | 2009-061895 | 5/2009 |
| WO | 2009-061902 | 5/2009 |
| WO | 2009-061907 | 5/2009 |

OTHER PUBLICATIONS

Chapman, B.; "Glow Discharge Processes—Sputtering and Plasma Etching"; John Wily & Sons, New York; 1980, p. 153 (3 total pgs).
ISA210 International Search Report for PCT/US2010/033884, dated Aug. 16, 2010, 5 pages.

* cited by examiner

APPARATUS AND METHOD FOR PLASMA TREATMENT OF CONTAINERS

CROSS REFERENCE TO RELATED APPLICATIONS

This application is a national stage filing under 35 U.S.C. 371 of PCT/US2010/033884, filed May 6, 2010, which claims priority to claims the benefit of U. S. Provisional Application Nos. 61/175,887, filed May 6, 2009; 61/175,898, filed May 6, 2009; and 61/320,361, filed Apr. 2, 2010; the disclosures of which are incorporated by reference herein in their entirety.

BACKGROUND

For some applications, it is desirable to plasma treat a container. For example, plasma treatment is useful for medicinal inhalation devices, including pressurized inhalers such as metered dose pressurized inhalers (MDIs) and dry powder inhalers (DPIs), which are widely used for delivering medicaments. The relatively high surface energy of materials typically used as containers for medicinal inhalation devices (e.g., deep drawn stainless steels or aluminum) can cause medicament particles in suspension formulations, for example, to adhere irreversibly to or adsorb onto the interior surface of the container. Such adhesion or adsorption can lead to a loss of potency and/or erratic dosing during the shelf-life of the device. Interaction between a container and a medicinal formulation can also potentially lead to enhanced medicament degradation or corrosion of the container.

While plasma treatment methods are known for modifying the surface properties of various articles, plasma treatment of containers continues to provide challenges.

SUMMARY

The present disclosure provides an apparatus and a method for plasma treatment of multiple containers. The apparatus and method disclosed herein utilize hollow, electrically-conductive nozzles, which serve as both at least partial electrodes (e.g., grounded electrodes) for plasma treatment and at least one of inlets or outlets for plasma-generating gas. During plasma treatment the nozzles extend into the containers to be treated, and, in some embodiments, the containers also serve as electrodes (e.g., radio frequency powered electrodes). In the apparatus and method disclosed herein, introducing or exhausting gas through the hollow electrodes favorably allows for uniformity of the treatment on the interior of a container, while the multiple hollow electrodes in the apparatus allow for multiple container interiors to be treated at the same time. The ability to treat multiple container interiors is more cost effective and requires shorter processing times than apparatuses and methods that 1) require an entire container (inside and outside) to be treated and/or 2) allow for treatment of only a single container at a time.

In one aspect, the present disclosure provides an apparatus for plasma treating multiple containers, the apparatus comprising:

a manifold comprising a first chamber with multiple outlet openings; and multiple hollow, electrically-conductive nozzles for at least one of delivering or exhausting plasma-generating gas, wherein the multiple hollow, electrically-conductive nozzles are connected to the multiple outlet openings and protrude from the manifold.

In another aspect, the present disclosure provides a method of plasma treating multiple electrically-conductive containers, the method comprising:

providing a reactor system comprising an apparatus disclosed herein;

inserting the multiple hollow, electrically-conductive nozzles into the multiple electrically-conductive containers;

grounding the multiple hollow, electrically-conductive nozzles while applying radio frequency power to the multiple electrically-conductive containers;

evacuating the multiple electrically-conductive containers;

providing a gas inside the multiple electrically-conductive containers; and generating a plasma to treat an interior surface of the multiple electrically-conductive containers, wherein at least one of evacuating or providing the gas is carried out through the hollow, electrically-conductive nozzles.

In the foregoing aspects, the apparatus is typically part of a capacitively coupled reactor system. In some embodiments of the foregoing aspects, the manifold further comprises a second chamber adjacent the first chamber, the second chamber comprising multiple passages therethrough aligned with the multiple outlet openings, wherein the multiple hollow, electrically-conductive nozzles extend through the multiple passages. In some embodiments, the multiple hollow, electrically-conductive nozzles extend through the multiple passages without sealing off the passages entirely. In these embodiments, each of the multiple passages in the second chamber includes a space (e.g., an unsealed space or physical gap) surrounding one of the hollow, electrically-conductive nozzles. In other embodiments, the multiple passages in the second chamber comprise sealing connections to the multiple hollow, electrically-conductive nozzles. In these embodiments, wherein the multiple passages in the second chamber are sealed off by the nozzles, typically a middle portion of each hollow, electrically-conductive nozzle has a central bore and at least two outer bores substantially parallel to the central bore, wherein the at least two outer bores tap into the second chamber. In some embodiments, the first chamber is connected to a gas supply, and the second chamber is connected to a vacuum source. In other embodiments, the first chamber is connected to a vacuum source, and the second chamber is connected to a gas supply.

We have found that plasma deposition methods and apparatuses that are configured to treat an entire container (inside and outside) tend to provide in some circumstances an undesirable number of containers that leak. The leakage is presumably due to a thick coating that can form on the brim of the container. The apparatus and method disclosed herein are configured to treat primarily an interior surface (i.e., at least a portion of the interior) of a container, eliminating the problem of excess coating on the brim. Advantageously, for at least some embodiments of the disclosure, plasma coatings can be deposited uniformly on the interior of a container. Uniform coating is facilitated by the coaxial electrode and gas inlet and/or outlet provided by the hollow, electrically-conductive nozzles and, in at least some embodiments, the central disposition of these nozzles inside the containers during treatment. Furthermore, in at least some embodiments, the present disclosure advantageously provides for uniform coating among multiple containers that are treated simultaneously. To favorably affect the coating uniformity among multiple containers, some embodiments of the present disclosure provide at least one of substantially uniform pressure among multiple containers, substantially equal gas flow paths into the containers, or substantially equal flow paths for exhausting gas from the containers.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. In particular, in some embodiments certain components may be present in interchangeable and/or identical multiples (e.g., pairs). For these components, the designation of "first" and "second" may be applied to the components merely as a matter of convenience in the description of one or more of the embodiments.

The term "plasma treatment" as used herein includes plasma etching, plasma priming, plasma deposition, and plasma polymerization. The apparatus and method disclosed herein are useful for each of these plasma processes. The term "plasma treatment" as used herein typically refers to plasma treatment carried out under conditions of ion bombardment.

The term "multiple" as used herein refers to more than one. Therefore, the apparatus disclosed herein includes at least two hollow, electrically-conductive nozzles (and corresponding outlet openings in the first chamber). The number of nozzles and corresponding outlet openings in the apparatus may be selected based on the size and design of the apparatus. In some embodiments, the apparatus includes up to 2500, or in some embodiments, any number between 2 and 2500 nozzles (and corresponding outlet openings in the first chamber) to plasma treat a corresponding number of containers. For example, the apparatus may include 2, 4, 8, 16, 32, 64, 128, 256, 512, or 1024 nozzles and corresponding outlet openings.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1A:
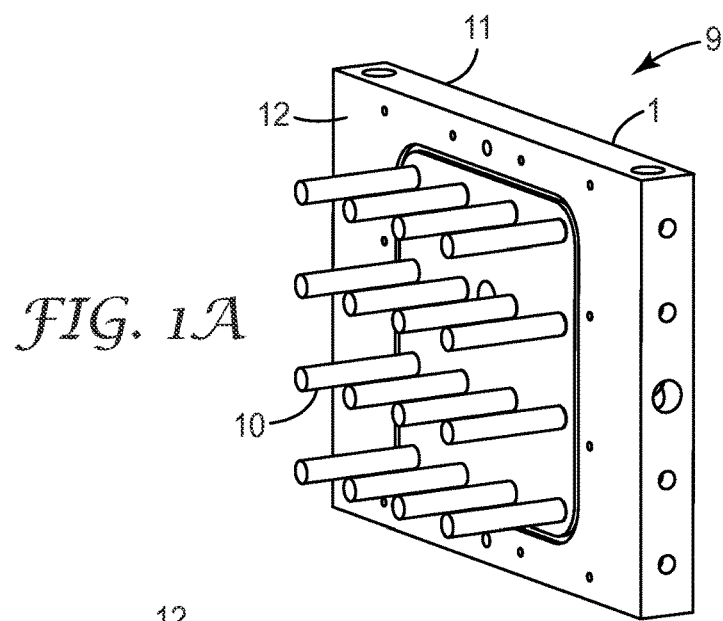
FIG. 1A is a perspective view of an exemplary embodiment of an apparatus according to the present disclosure.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Figure 1B:
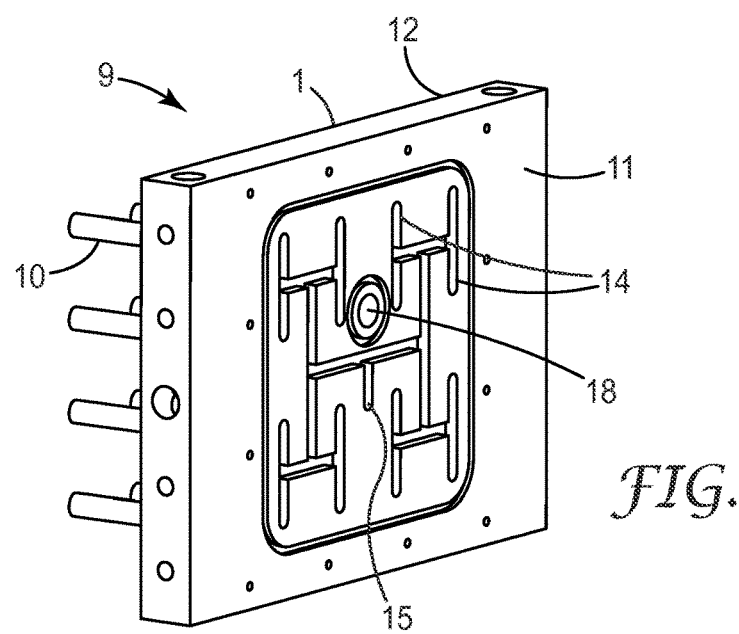
FIG. 1B is a perspective view of the opposite face of the exemplary embodiment shown in FIG. 1A.

An apparatus 9 for plasma treating multiple containers is shown in FIGS. 1A and 1B. Apparatus 9 can be useful, for example, as a component of apparatus 90 shown in FIG. 4. In the illustrated embodiment, manifold 2 comprises a first plate 1 having a first face 11 and a second face 12. Multiple hollow, electrically-conductive nozzles 10 are connected to multiple outlet openings (not shown) in the first plate 1 and protrude from the second face 12 of the first plate 1. For example, the nozzles 10 may be press fit into the outlet openings in the first plate, or they may be sealed into the outlet openings (e.g., using o-rings). The first chamber in manifold 2 comprises a first plurality of pathways 14 in the first face 11 of the first plate 1 for connecting the multiple hollow, electrically-conductive nozzles 10 to a supply of plasma-generating gas or a vacuum source (not shown). The first plate 1 illustrated in FIG. 1B also includes port 18 extending therethrough. Port 18 is adapted to connect to a supply of plasma-generating gas or a vacuum source (not shown). The first plate 1 can therefore be useful in a manifold that further includes a second chamber as described below in reference to FIGS. 3 and 4.

The port 18 through the first plate 1 may be the same size on the first and second faces 11 and 12, or the size may increase or decrease between the first and second faces. In some embodiments, the size of the port is larger on the second face 12 of the first plate 1. For example, on the first face 11, the port may be offset from the center of the first plate 1, while on the second face 12, the port may be larger and include the center (i.e., the geometric center).

In some embodiments, including the embodiment illustrated in FIG. 1B, the first chamber comprises non-linear pathways (e.g., tortuous pathways) that connect the hollow, electrically-conductive nozzles to a gas supply or vacuum source. In some embodiments, including the embodiment illustrated in FIG. 1B, the first plurality of pathways 14, is configured such that each pathway between one nozzle of the multiple hollow, electrically-conductive nozzles 10 and the supply of plasma-generating gas or vacuum source (not shown) is substantially the same in gas flow path volume. The phrase "substantially the same in gas flow path volume" means that individual pathways 14 may differ in volume by up to 10 (in some embodiments, up to 8, 6, 5, 2, or 1) percent. In some embodiments, each pathway between one nozzle of the multiple hollow, electrically-conductive nozzles 10 and the supply of plasma-generating gas or vacuum source (not shown) is substantially the same (in some embodiments, within 10, 8, 6, 5, 2, or 1 percent) in diameter. In some embodiments, each pathway between one nozzle of the multiple hollow, electrically-conductive nozzles 10 and the supply of plasma-generating gas or vacuum source (not shown) is substantially the same (in some embodiments, within 10, 8, 6, 5, 2, or 1 percent) in length. In the illustrated embodiment, a supply of plasma-generating gas or vacuum source is accessible through channel 15. The first plurality of pathways 14 is configured such that each pathway between one nozzle of the multiple hollow, electrically-conductive nozzles 10 and channel 15 is substantially the same in both gas flow path volume and length. This configuration is accomplished by use of the H patterns shown in FIG. 1B. In some embodiments, the depth and width of channel 15 are greater than or equal to the depths and widths of the sides (i.e., arms) of the H patterns.

Figure 2:
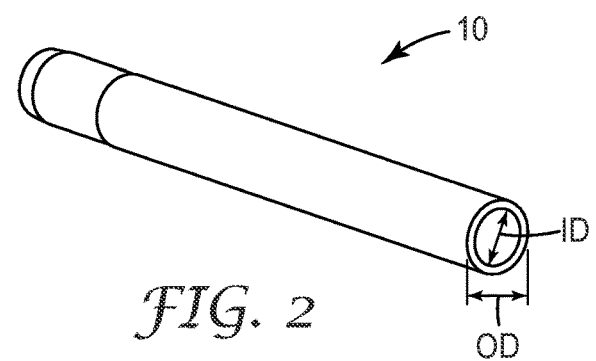
FIG. 2 is a perspective view of a hollow, electrically-conductive nozzle useful in some embodiments of an apparatus according to the present disclosure.

An exemplary hollow, electrically-conductive nozzle 10, useful as a component of an apparatus disclosed herein, is shown FIG. 2. The illustrated nozzle may be useful, for example, as a component of apparatus 9 or 90, shown in FIGS. 1A, 1B, and 4. The size of the nozzle 10 may be selected based on the size of the container to be treated. Prescription MDIs typically include canisters with openings having diameters of about 20 mm although the apparatus and method disclosed herein are not limited to treating containers of this size.

The illustrated nozzle 10 has an inner diameter (ID) and an outer diameter (OD). The outer diameter (OD) of the nozzle 10 should be such that the nozzle 10 will fit into the container to be treated. For example, the outer diameter (OD) of nozzle 10 may be at least 0.125, 0.15, 0.175, 0.20, 0.225, 0.25 or 0.26 inches (3.2, 3.8, 4.4, 5.1, 5.7, 6.35 or 6.6 mm) and may be up to 0.31, 0.32, 0.35, 0.375, 0.4, 0.425, 0.45, 0.475, or 0.5 inches (7.9, 8.1, 8.9, 9.5, 10.2, 10.8, 11.4, 12.1, or 12.7 mm). In some embodiments, the outer diameter is in a range from 0.125 to 0.5 inches (3.2 mm to 12.7 mm), 0.225 to 0.375 inches (5.7 mm to 9.5 mm), or 0.25 to 0.35 inches (6.35 mm to 8.9 mm). In some embodiments, the inner diameter (ID) of nozzle 10 may be at least 0.0625, 0.08, 0.10, 0.125, 0.15, 0.175, 0.20, 0.235, or 0.24 inches (1.6, 2.0, 2.5, 3.2, 3.8, 4.4, 5.1, 6.0, or 6.1 mm) and may be up to 0.28, 0.30, 0.32, 0.35, 0.4, 0.425, 0.45, 0.475, or 0.48 inches (7.1, 7.6, 8.1, 8.9, 10.2, 10.8, 11.4, 12.1, or 12.2 mm). In some embodiments, the inner diameter is in a range from 0.0625 to 0.48 inches (1.6 mm to 12.2 mm), 0.125 to 0.35 inches (3.2 mm to 8.9 mm), or 0.2 to 0.32 inches (5.1 mm to 8.1 mm). The inner diameter may be selected based on the thickness of the material used to make the nozzles. However, if the inner diameter is less than 0.0625 inches (1.6 mm), depending on the penetration of the nozzle into the container, the bottom of the container may be treated excessively in comparison to other interior portions of the container, which may result in non-uniform plasma treatment. In some embodiments, the ratio of the outer diameter (OD) to the inner diameter (ID) is in a range from 8:1 to 1.04:1, 5:1 to 1.1:1, or 3:1 to 1.5:1.

Figure 3A:
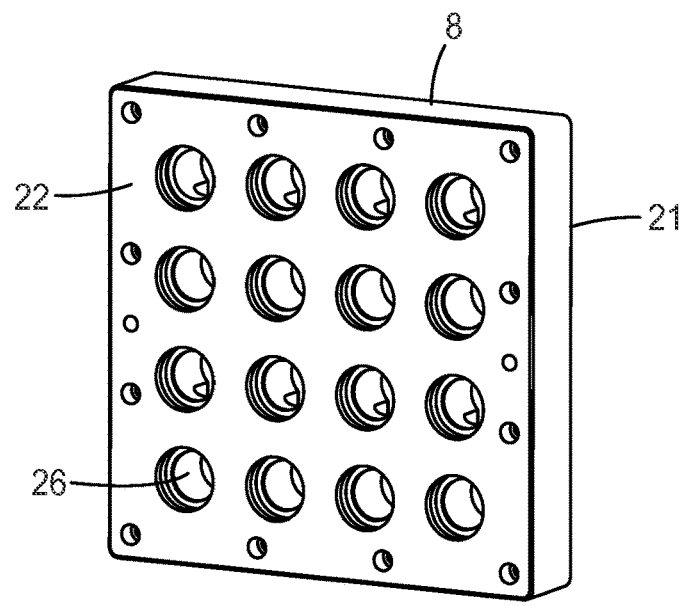
FIG. 3A is a perspective view of an exemplary embodiment of a second chamber component useful in some embodiments of an apparatus according to the present disclosure.
Figure 3B:
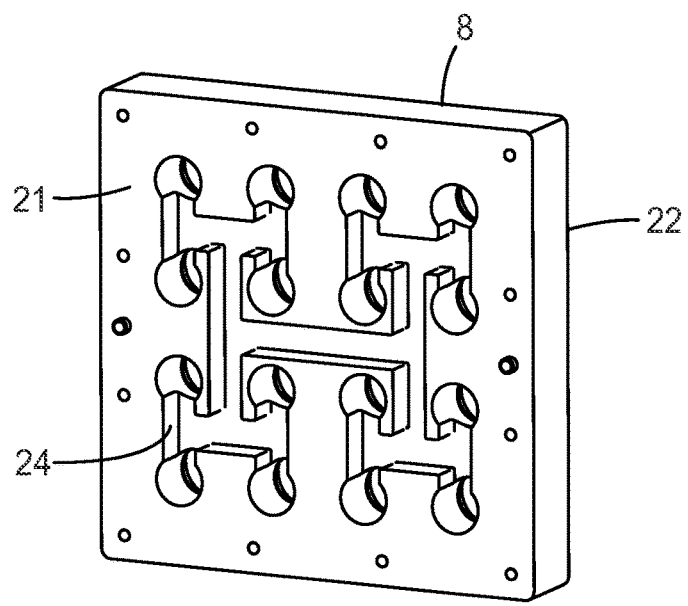
FIG. 3B is a perspective view of the opposite face of the exemplary embodiment shown in FIG. 3A.

FIGS. 3A and 3B illustrate an electrically insulating block 8 that can be coupled to the first plate 1 shown in FIGS. 1A and 1B to provide another exemplary embodiment of a useful manifold for the apparatus according to the present disclosure. In the illustrated embodiment of FIG. 3B, the first face 21 of insulating block 8 has a plurality of interconnected pathways 24. The first face 21 of the insulating block 8 is disposed on (e.g., joined or sealed to) the second face 12 of the first plate 1, so that the second plurality of interconnected pathways 24 is in communication with port 18 in first plate 1. The second plurality of interconnected pathways 24 extend to discrete openings 26 in a second face 22 of insulating block 8 (shown in FIG. 3A). The multiple hollow, electrically-conductive nozzles 10 pass through insulating block 8 and extend out of the discrete openings 26 in the second face 22 of insulating block 8.

In some embodiments, including the embodiment illustrated in FIG. 3B, the second chamber in the manifold comprises a second plurality of interconnected pathways, which may be non-linear pathways (e.g., tortuous pathways). In the embodiment illustrated in FIG. 3B, the second plurality of interconnected pathways 24 is configured such that each pathway between one of the discrete openings 26 and the port 18 in the first plate 1 has substantially the same volume and length. This configuration can be accomplished by use of the H patterns shown in FIG. 3B. The phrase "substantially the same in volume" means that individual pathways 24 may differ in volume by up to 10 (in some embodiments, up to 8, 6, 5, 2, or 1) percent. In some embodiments, each pathway between one nozzle of the multiple hollow, electrically-conductive nozzles 10 and port 18 is substantially the same (in some embodiments, within 10, 8, 6, 5, 2, or 1 percent) in diameter. The phrase "substantially the same in length" means that individual pathways 24 between one nozzle of the multiple hollow, electrically-conductive nozzles 10 and port 18 is may differ in length by up to 10 (in some embodiments, up to 8, 6, 5, 2, or 1) percent.

Figure 4:
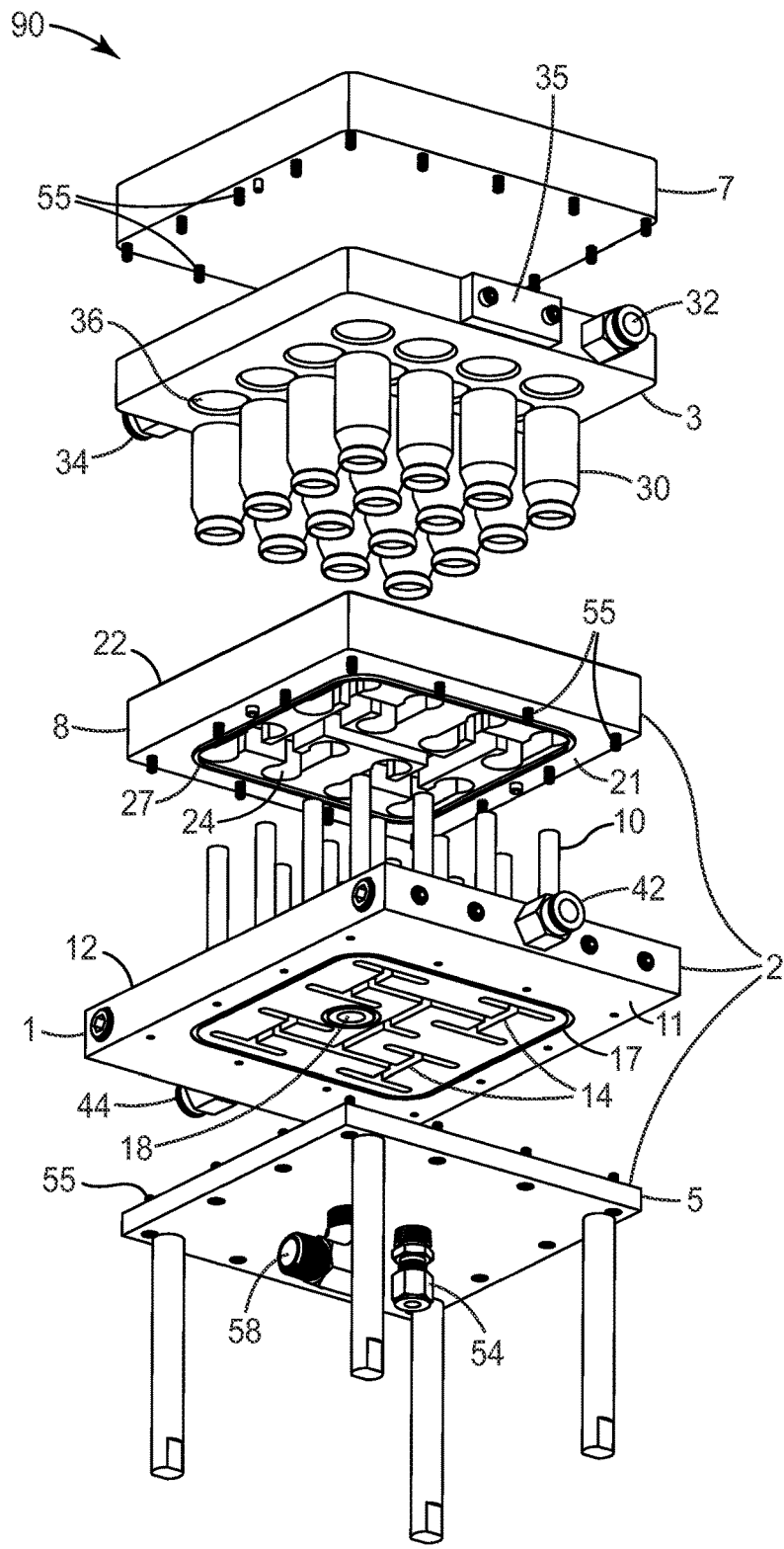
FIG. 4 is an exploded perspective view of an exemplary embodiment of an apparatus according to the present disclosure.

FIG. 4 illustrates an exploded view of an exemplary apparatus 90 according to the present disclosure, which apparatus 90 includes a manifold 2 that comprises the first plate 1 and multiple nozzles 10 shown in FIGS. 1A and 1B and insulating block 8 shown in FIGS. 3A and 3B. Apparatus 90 further comprises base 5 that is disposed on (e.g., joined or sealed to) the first face 11 of first plate 1. The base 5 can be connected to the first face 11 of the first plate 1 optionally using bolts 55 or other fasteners. Similarly, the first face 21 of electrically insulating block 8 can be connected to the second face 12 of the first plate 1 optionally using bolts 55 or other fasteners. Base 5 has two connectors 54 and 58, one for attachment to a high pressure gas supply and one for attachment to a vacuum source. Connector 54 is aligned with channel 15 leading to the first plurality of pathways 14. The base 5 and first plurality of pathways 14 in the first face 11 of the first plate 1 together define the first chamber of manifold 2. The first chamber can optionally be sealed, for example, using an o-ring in slot 17. Connector 58 is aligned with port 18 that extends through first plate 1 and is in communication with second plurality of interconnected pathways 24 in insulating block 8. The second plurality of interconnected pathways 24 and second face 12 of the first plate 1 together define the second chamber of manifold 2, which can optionally be sealed, for example, using an o-ring in slot 27.

Apparatus 90 further comprises second plate 3 comprising slots 36 for multiple containers 30. Slots 36 are aligned with the discrete openings 26 in the second face of the insulating block 8, shown in FIG. 3A. Second plate 3 also has a connection 35 for a radio frequency (RF) power source so that RF power can be supplied to the multiple containers 30.

Referring again to FIG. 3A, discrete openings 26 each may have a sealing means (e.g., o-ring) to connect to one of the multiple containers 30, or the insulating base 8 may comprise a material that allows for a sealing connection when the multiple containers 30 are pressed into the discrete openings 26. In some embodiments, discrete openings 26 each also have a metal washer (not shown) that reinforces the opening. The metal washer is made from a material (e.g., stainless steel) that provides a strong surface on which each container can be sealed. Without wishing to be bound by theory, it is also believed that the metal washer can also enhance the electric field near the opening of the container to help enhance the coating near the opening. The presence of the metal washer can also reduce the arcing that can occur at the brim of the container 30, and any arcing that may occur can arc to the metal washer, thereby preventing damage to the container 30.

For plasma treatment methods according to the present disclosure in connection with the embodiment illustrated in FIG. 4, 16 containers can be lowered onto insulating block 8 so that the brim of each container is in contact with the second face 22 of the insulating block 8 and so that a seal is created between each container at the discrete opening 26. In this configuration, the 16 nozzles 10 extend into the 16 containers 30. Voltage can be applied to the containers and the nozzles grounded to create the plasma and an ion sheath within the interior of the container, in order to treat the interior of the containers. In some embodiments, to provide a gas flow through the containers, the containers can be continuously evacuated via the second plurality of interconnected pathways 24 while gas is supplied into the containers through nozzles 10. In other embodiments, the containers can be continuously evacuated via the nozzles 10 while gas is supplied into the containers from port 18 through second plurality of interconnected pathways 24.

In some embodiments, methods according to the present disclosure comprise controlling the temperature of at least one of the multiple hollow, electrically-conductive nozzles or the multiple electrically-conductive containers while generating plasma. Controlling the temperature can be carried out, for example, by passing a coolant through the flow paths described below in reference to FIGS. 4 and 5. The coolant may be a gas (e.g., air) or a liquid (e.g., water). The temperature during plasma generation can advantageously be maintained below the melting point of the material used to make the nozzles or containers but above the dew point so that condensation does not occur on the nozzles or containers.

In the embodiment illustrated in FIG. 4, apparatus 90 further comprises top base 7, which is typically made from an insulating material. In some embodiments, when top base 7 and second plate 3 are joined together, for example, using screws 55, they together define an interior pocket (not shown) through which coolant can pass to cool the second plate 3 and the multiple containers 30 during plasma treatment. Coolant may flow into coolant entrance port 34 and out of coolant exit port 32 or the direction of flow may be reversed. The second plate 3 can include flow paths for coolant (not shown) extending between the coolant entrance port 34 and the coolant exit port 32. These flow paths may surround the impressions made by slots 36 in the second plate 3.

Figure 5:
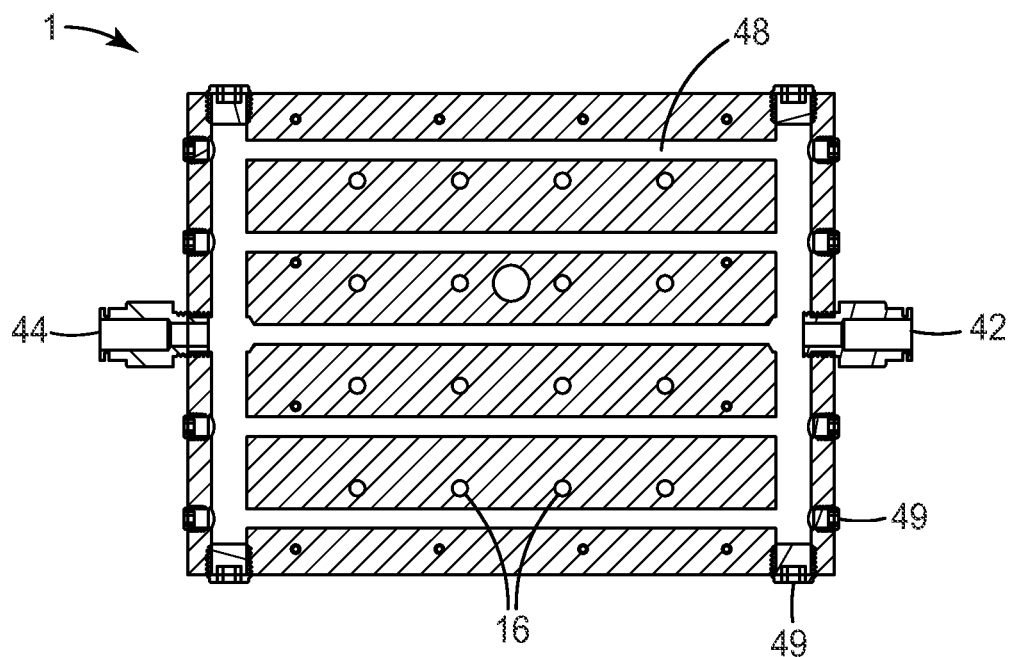
FIG. 5 is a plan view of optional, interior cooling channels included in the exemplary embodiment shown in FIGS. 1A and 1B.

Cooling first plate 1 during plasma treatment may also be useful. In the embodiment illustrated in FIG. 4, first plate 1 comprises a coolant entrance port 42 and a coolant exit port 44 with flow paths for coolant extending between the coolant entrance port and the coolant exit port. Exemplary flow paths 48 are shown in FIG. 5. The flow paths 48 can be formed to extend through the first plate 1, and caps 49 can be used to close the openings around the perimeter of the first plate 1. In the illustrated embodiment, flow paths 48 are configured to pass between the multiple openings 16 for receiving the multiple hollow, electrically-conductive nozzles 10 in the first plate 1. In this configuration, coolant that is passed through the flow paths can cool both first plate 1 and nozzles 10.

Controlling the temperature of at least one of the multiple hollow, electrically-conductive nozzles or the multiple electrically-conductive containers while generating plasma can also be accomplished using methods external to the apparatus. For example, the containers can be fan-cooled during plasma generation. Controlling the temperature of the nozzles is typically advantageous for plasma etching and may also be advantageous during plasma deposition.

Figure 6:
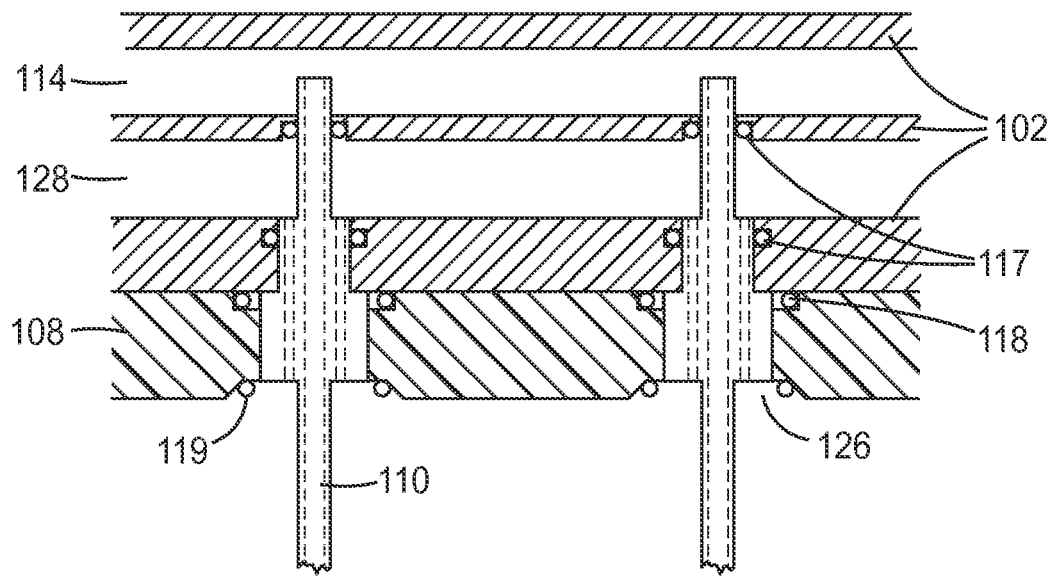
FIG. 6 is a partial cross-sectional side view of another exemplary embodiment of an apparatus according to the present disclosure.

A cross-sectional side view of a portion of another exemplary apparatus for plasma treating multiple containers is shown in FIG. 6. The apparatus includes a manifold 102 having two generally horizontal first and second chambers 114 and 128, respectively. In some embodiments, chamber 114 is connected to a gas feed/supply system, and chamber 128 is connected to a vacuum source. In some embodiments, chamber 128 is connected to a gas feed/supply system, and chamber 114 is connected to a vacuum source. The manifold includes vertical passages with appropriate seal systems 117 (e.g., o-rings) to allow for sealing-connection to nozzles 110. The apparatus also includes insulating block 108 having discrete vertical openings 126 extending from a first face to a second face and fitted below the manifold so that the discrete openings are aligned with the vertical passages. The insulating block also has appropriate seal systems 118 (e.g., o-rings) for sealing to manifold 102.

Figure 7:
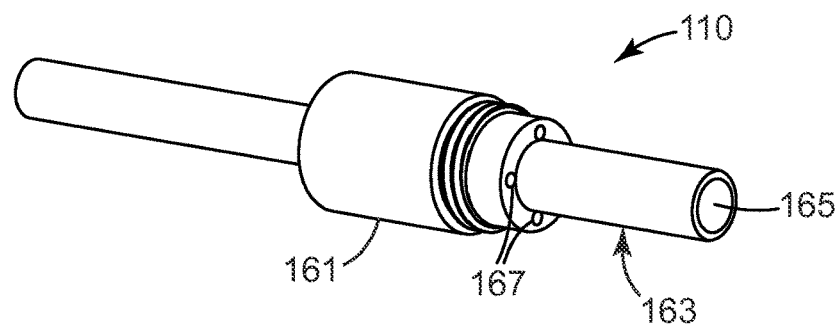
FIG. 7 is a perspective view of a hollow, electrically-conductive nozzle useful for the embodiment shown in FIG. 6.

In the embodiment illustrated in FIGS. 6 and 7, the apparatus includes hollow, electrically-conductive nozzles 110, each of which comprises a middle portion 161 and two extensions 163 on opposite ends of the middle portion 161. The nozzle includes a central bore 165 and outer bores 167 substantially parallel to the central bore, wherein the central bore 165 runs through the extensions and the middle portion, and the outer bores 167 run through the middle portion 161. One end of each nozzle 110 is inserted through the insulating block 108 into the manifold 102 so that the respective opening of the central bore 165 taps into chamber 114 and the respective openings of the outer bores 167 tap into chamber 128. One extension 163 of nozzle 110 seals one of the outlet openings of chamber 114. The middle portion 161 of each nozzle 110 seals one of the passages from chamber 128 and is also sealed within the insulating block 108. The nozzle 110 can be screwed into manifold 102 using the illustrated threads. The openings of the outer bores 167 are substantially flush with the lower surface of the insulating block 108, and the central bore 165 extends beyond the lower surface of the insulating block 108. In the embodiment illustrated in FIG. 6, a sealing system 119 is provided on the lower side of insulating block 108 near the block/nozzle conjunction to allow for a sealing-connection to the container to be treated.

For hollow, electrically-conductive nozzle 110 illustrated in FIG. 7, the middle portion 161 has four outer bores 167 surrounding the central bore 165; however, only three outer bores 167 are visible in the perspective view. In other embodiments, 2, 3, 5, 6, or more outer bores 167 surround the central bore 165. Typically, the outer bores 167 are evenly distributed around the central bore 165. The extensions 163 including central bore 165 of hollow, electrically-conductive nozzle 110 may have any of the inner diameters, outer diameters, and ratios of outer diameter to inner diameter described above for hollow, electrically-conductive nozzle 10. The inner diameter of the outer bores 167 should be large enough to allow introduction or exhaustion of gas to or from the container to be treated. In some embodiments, the inner diameter of outer bores 167 is in a range from 0.03125 to 0.25 inches (0.8 mm to 6.35 mm), 0.047 to 0.125 inches (1.2 mm to 3.2 mm), or 0.05 to 0.1 inches (1.3 mm to 2.5 mm).

Figure 8:
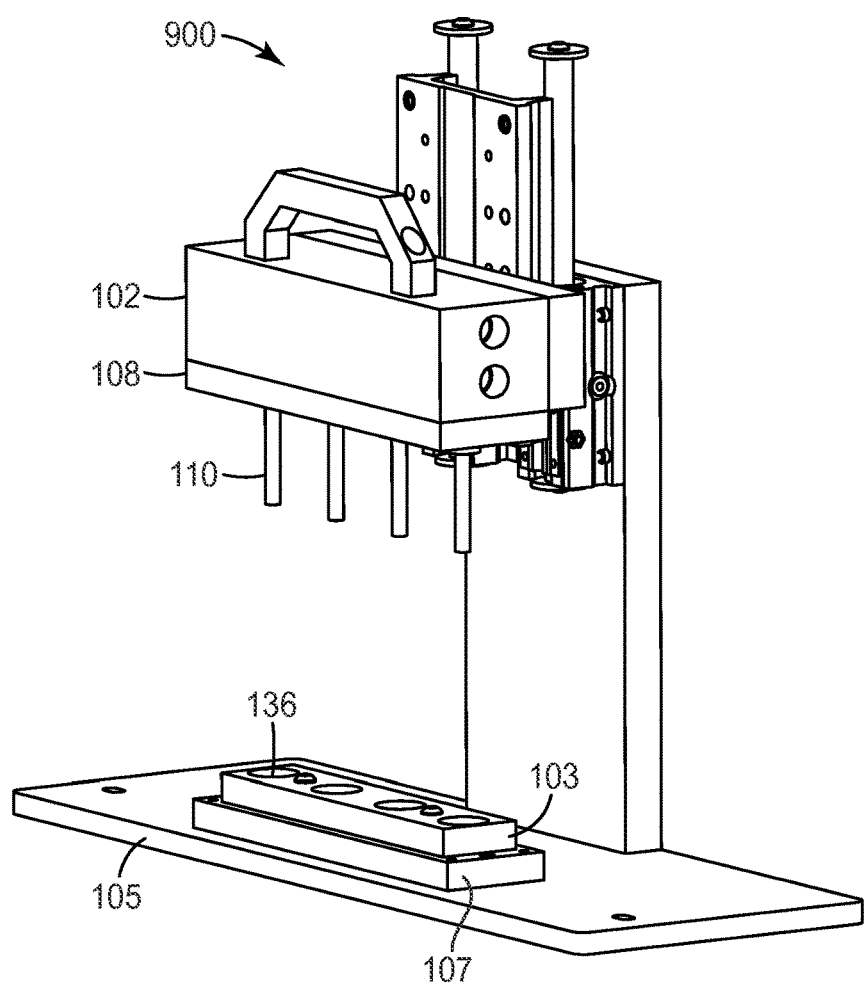
FIG. 8 is a perspective view of another exemplary embodiment of an apparatus according to the present disclosure.

FIG. 8 illustrates a perspective view of exemplary apparatus 900 according to the present disclosure, which apparatus 900 includes manifold 102, insulating block 108, and multiple nozzles 110 as shown in cross-section in FIG. 6. Apparatus 900 further comprises second plate 103 comprising slots 136 for multiple containers (not shown). Slots 136 are aligned with the discrete openings 126 in the second face of the insulating block 108, shown in FIG. 6. Second plate 103 also has a connection for a radio frequency power source (not shown) so that RF power can be supplied to the multiple containers. In the illustrated embodiment, second plate 103 is disposed on a second insulating block 107 that is in turn disposed on a grounded base 105.

For plasma treatment methods according to the present disclosure in connection with the embodiment illustrated in FIG. 8, the four nozzles 110 can be lowered into four containers so that the upper edge of the brim of each container is in contact with the lower side of the middle portion 161 of nozzle 110 and so that a seal is created between each container (outer surface of brim) and the outer lower surface of the insulating block 108. Voltage can be applied to the containers and the nozzles grounded to create the plasma and an ion sheath within the interior of the container, in order to treat the interior of the containers. To provide a gas flow through the containers, the containers can be continuously evacuated via the outer bores 167 (inlet openings near the brim) while gas is supplied into the containers via the central bore 165, or vice versa.

For the embodiment illustrated in FIG. 8, at least one of the insulating block 108 or second insulating block 107 can be provided with a coolant entrance port and a coolant exit port with flow paths for coolant extending between the entrance port and the exit port as described above for the embodiment illustrated in FIGS. 4 and 5. The flow paths for coolant may provide a means for cooling at least one of the nozzles or the containers during plasma treatment. Apparatus 900 can also be cooled by external means (e.g., fans).

Various materials may be useful for constructing exemplary apparatuses illustrated in FIGS. 1 to 8. Base 5; first plate 1; second plate 3, 103; and manifold 102 are typically made from electrically-conductive materials (e.g., metals such as aluminum, copper, and stainless steel). Insulating block 8, 108; top base 7; and second insulating block 107 are typically made from electrically insulating materials, for example, plastics (e.g., polytetrafluoroethylene, polyetheretherketone, polyetherketone, and polyetherimide) and ceramics. In some embodiments, electrically insulating materials useful for making insulating portions of the apparatus disclosed herein are made from polyetherimide, (available under the trademark "ULTEM" (grade 1000) of General Electric Company and available from many suppliers worldwide).

Various materials (e.g., aluminum, stainless steel, copper, or graphite) may be useful for making the hollow, electrically-conductive nozzles 10, 110 useful for practicing the present disclosure. In some embodiments, the nozzles are made from aluminum or an aluminum alloy. Aluminum is a useful material in part because of its low sputter yield, which means that it provides very little contamination on surfaces to be plasma treated.

In some embodiments, the hollow, electrically-conductive nozzles 10, 110 are provided with a surface dielectric coating, which may protect against etching and improve durability. In some embodiments, the hollow, electrically-conductive nozzles 10, 110 are provided with surface anodization. Anodizing is beneficial in hardening, for example, the aluminum or aluminum alloy as well as removing or minimizing surface imperfections resulting from fabrication (such as deep drawing) and facilitating the naturally occurring oxide process, all of which facilitate overall durability of the nozzle. The anodization can be carried out to a depth of up to 0.002 or 0.0015 inches (0.05 mm or 0.038 mm), in some embodiments, a depth of at least 0.0005 or 0.001 inches (0.013 mm or 0.025 mm). The anodization may a total thickness of up to 0.004 inches (0.10 mm) (in some embodiments, up to 0.003, 0.002, or 0.001 inches (0.076 mm, 0.05 mm, or 0.025 mm)). Conveniently, for the embodiment illustrated in FIGS. 1A and 1B, anodization can be carried out after the nozzles are connected to (e.g., pressed into) first plate 1.

In some embodiments, including those illustrated in FIGS. 1A, 1B, 4, 5, 6, and 8, the multiple outlet openings (16, 126) and the multiple hollow, electrically-conductive nozzles 10, 110 are arranged in a corresponding, regular pattern. In other words, the multiple outlet openings may be an array of outlet openings that is connected to an array of hollow, electrically-conductive nozzles 10, 110. The array may be linear or two dimensional. The array of nozzles 10 may be useful for uniformly plasma treating an array of containers, for example, by enabling uniform pressures among the containers in the array, described in further detail below.

For the apparatus and method according to the present disclosure, the hollow, electrically-conductive nozzles 10, 110 protrude from manifold 2, 102, as illustrated in FIGS. 1A, 1B, 4, 6, and 8. For the embodiments shown in FIGS. 1A and 1B, nozzles 10 protrude from first plate 1. For the embodiments shown in FIGS. 4, 6, and 8, nozzles 10, 110 protrude from insulating block 8, 108. The hollow, electrically nozzles 10, 110 protrude from the manifold in an apparatus disclosed herein so that they are able to extend into the interiors of multiple containers.

The length of the nozzles and the portion that protrudes from the manifold can be adjusted depending on the size of the container to be treated. Each container has a distance between a brim and a bottom. For prescription MDI containers, this distance can be 2.33 inches (5.9 cm), 1.275 inches (3.2 cm), or 1.22 inches (3.1 cm) or in a range from 1.2 inches to 2.5 inches (3.0 cm to 6.35 cm). However, the apparatus and method disclosed herein are not limited to treating containers of this size. In some embodiments the hollow, electrically-conductive nozzles penetrate into the containers in a range from 30 percent to 99 percent of the distance between the brim and the bottom. The percent penetration may be calculated as the distance between the container brim and tip of the nozzle divided by the distance between the brim and the bottom of the container, with the quotient multiplied by 100. In some embodiments, the hollow, electrically-conductive nozzles penetrate into the containers at least 30, 35, 40, 45, or 50 percent up to 95, 96, 97, 98, or 99 percent. Enhanced gas flow and plasma generation may result when the nozzles penetrate into the containers in a range from 30 percent to 99 percent, which may enhance the uniformity of the plasma treatment within a container. Furthermore, the distance between a tip of the nozzle and the bottom of the container may, in some embodiments, be in a range from 0.0625 inches (1.6 mm) up to 1.5 inches (38 mm), depending on the size of the container.

Various modifications of the illustrated embodiments of FIGS. 1A through 8 are envisioned. For example, a nozzle 10 as shown in FIG. 2 can be useful in the apparatus shown in FIGS. 6 and 8. With such a substitution, the lower portion of manifold 102 and insulating block 108 can be modified such that there is a space (e.g., an unsealed space or physical gap) surrounding the nozzle allowing communication between chamber 128 and a container attached at opening 126. The space can be achieved, for example, by making the openings 126 in the insulating block 108 and the lower portion of manifold 102 larger in circumference than the nozzles and eliminating the seals around the nozzles in these areas. Furthermore, the apparatus of FIG. 8 can be modified to have a two-dimensional array instead of the illustrated linear array, and the apparatus of FIG. 4 can be modified to have a linear array instead of the illustrated two-dimensional array. The apparatuses of the illustrated embodiments can also be modified to have any number of hollow, electrically-conductive nozzles, as described above.

Furthermore, other hollow, electrically-conductive nozzles may be useful in the apparatus and method according to the present disclosure. For example, the hollow, electrically-conductive nozzle for at least one of delivering or exhausting plasma-generating gas may be a partial electrode that has a coaxially disposed solid electrode, for example, through its center. In some embodiments, the coaxially disposed solid electrode may penetrate further into the container than the hollow nozzle portion. In other embodiments, the bottom of the coaxially disposed solid electrode may be flush with the bottom of the hollow nozzle portion. Or the coaxially disposed solid electrode may be shorter than the hollow nozzle portion.

For the apparatuses 90, 900 shown in FIGS. 4 and 8, individual containers 30 (not shown in FIG. 8) serve as the powered electrode. Therefore, for FIG. 4, 16 individual plasma generators are formed when each of the nozzles 10 is grounded and each of the containers 30 is powered. Similarly, in FIG. 8, four individual plasma generators are formed. In embodiments wherein an individual container serves as a powered electrode, the container typically has a sealing connection (e.g., using an o-ring or other seal material) to the manifold around an individual hollow, electrically-conductive nozzle. In embodiments wherein the individual containers serve as electrodes, the containers can be made, for example, of aluminum, an aluminum alloy, or stainless steel, and the interior surface of the containers may be anodized or formed with another dielectric coating as described above. Typically the hollow, electrically-conductive nozzles are centrally disposed in the electrically-conductive containers. Centrally disposed typically means that a hollow, electrically-conductive nozzle occupies a space including the geometric center of the container. In some embodiments, centrally disposed refers to the hollow, electrically-conductive nozzle and the electrically-conductive container being coaxial.

It is also envisioned that the apparatus according to the present disclosure may be useful, for example, as a portion of a parallel plate plasma generator. Accordingly, in some embodiments, the apparatus according to the present disclosure further comprises an evacuable chamber joined to the manifold, wherein the multiple hollow, electrically-conductive nozzles extends into the evacuable chamber, and an electrically-conductive plate within the evacuable chamber in proximity to the multiple hollow, electrically-conductive nozzles, wherein the conductive plate comprises a connection for a radio frequency power source. A configuration similar to that described in International Pat. App. Pub. No. WO 2009/061895 (Jinks et al) and schematically illustrated in FIG. 6 of that reference may be useful. For example, the containers may be placed inside a chamber on an RF powered electrode plate that is isolated from the chamber by an insulating block. In operation, the electrically-conductive plate can hold multiple containers to be treated, and the hollow, electrically-conductive nozzles can be lowered into the containers typically without forming a seal between the manifold and the containers. RF power can be applied to the conductive plate, and the nozzles can be grounded during plasma generation. In some of these embodiments, a modification of the apparatus shown in FIGS. 6 and 8 may be useful. For example, the manifold 102 may be modified to have only one chamber, and a nozzle 10 such as that shown in FIG. 2 may be used. Furthermore, an apparatus 9 shown in FIGS. 1A and 1B can be disposed on a vacuum chamber so that the nozzles extend into the chamber. For these embodiments, the containers may be made from aluminum, an aluminum alloy, or stainless steel as described above, and they can also be made, for example, from glass, plastic (e.g. polyethylene terephthalate, polycarbonate, polyethylene, high density polyethylene and polypropylene) and ceramics.

In the method according to the present disclosure, an RF electric field is applied to the powered electrode (e.g., either the container or a plate electrode on which the containers are placed), ionizing the gas and establishing a plasma. In the RF-generated plasma, energy is coupled into the plasma through electrons. The plasma acts as the charge carrier between the electrodes. In some embodiments, the plasma may be visible as a colored cloud. The plasma is also generally thought to form an ion sheath proximate at least to the RF-powered electrode. The ion sheath may appear as a darker area near the RF-powered electrode. The depth of the ion sheath normally ranges from about 1 mm to about 50 mm and depends on factors such as the type and concentration of gas used, pressure, the spacing between the electrodes, and relative size of the electrodes. For example, reduced pressures will increase the size of the ion sheath. When the electrodes are different sizes, a larger, stronger ion sheath will form around the smaller electrode. Generally, the larger the difference in electrode size, the larger the difference in the size of the ion sheaths, and increasing the voltage across the ion sheath will increase ion bombardment energy.

Plasma, created from the gas within the container, can be powered by an RF generator (e.g., available from Seren IPS, Inc., Vineland, N.J., Model No. R1001) operating at a frequency in a range, for example, from 0.001 to 100 MHz). The RF generator (e.g., an oscillator) can provide power at a typical frequency in a range from 0.01 to 50 MHz, for example, 13.56 MHz or any whole number (e.g., 1, 2, or 3) multiple thereof. The power source may be connected to the apparatus (e.g., at connection 35) via a network that serves to match the impedance of the power supply with that of the transmission line to effectively transmit RF power through a coaxial transmission line. Such matching networks are commercially available (e.g., from Advanced Energy, Fort Collins, Colo., as Rf Plasma Products Model AMN-10).

As described above, the apparatus and method according to the present disclosure are useful for a variety of plasma treatment processes. For the application of medicinal inhalation devices, the apparatus and method disclosed herein may be useful, for example, for plasma priming and plasma deposition of a non-metal coating on the inside of a container.

In some embodiments, the plasma treatment method according to the present disclosure includes plasma priming (e.g., by oxygen or argon plasma). For example, the method includes treating the interior surface of a container with oxygen plasma under conditions of ion bombardment. Typically for plasma priming, power densities in the range from about 0.10 to about 0.95 watts/square cm can be applied. Also, typically for plasma priming, flow densities of the priming gas in the range from about 0.01 to about 1 sccm/square cm, in some embodiments 0.05 to 1 about sccm/square cm, and in some embodiments, about 0.1 to about 0.6 sccm/square cm can be applied. Power density is a ratio of the plasma power (typically in watts) and the surface area (typically in square cm) of the substrate to be treated (i.e. the density of plasma power at or upon the surface to-be-coated). Similarly flow density is a ratio of the flow (typically in standard cubic centimeters per minute (sccm)) of the gas and the surface area of the substrate to be treated. Before plasma priming, the interior surfaces of the containers can be solvent washed (e.g., with an organic solvent such as acetone or ethanol).

In some embodiments, the plasma treatment method according to the present disclosure includes depositing diamond-like glass on the interior surface of the container. Diamond-like glass coatings are coatings comprising carbon, silicon, hydrogen, and oxygen typically provided by plasma deposition under conditions of ion bombardment. In these embodiments, a gas comprising one or more organosilicon compounds is introduced into the system at a flow rate selected so that a sufficient flow is provided to establish a suitable pressure at which to carry out plasma deposition. In some embodiments, the pressure at the interior surface of the container is at least 100 millitorr (13.3 Pa) or 300 millitorr (40 Pa), and in some embodiments is in the range from 500 millitorr to 5000 millitorr (66.7 Pa to 667 Pa). In some embodiments, the flow density of the organosilicon compound applied is at least about 0.01 sccm/square cm, in some embodiments at least about 0.05 sccm/square cm, and in some embodiments at least about 0.1 sccm/square cm. Flow densities are typically up to about 0.30 sccm/square cm, in some embodiments up to about 0.25 sccm/square cm. These flow densities typically refer to organosilicon compounds only (i.e., without any non-organosilicon assist gases). The organosilicon compound may be a mixture of organosilicon compounds. These pressures and flow densities may be advantageous in providing superior coating densities as well as uniform and conformal coatings having a high degree of flexibility and resistance to cracking Favorably the plasma density is greater than about 0.10 watts/square cm. It has been found advantageous in facilitating the provision of flexible coatings, to apply lower power density in combination with longer deposition times.

For plasma deposition of diamond-like glass, typically elemental silicon present in the at least one organosilicon compound is present in an amount of at least about 5 atomic percent of the gas mixture. In some embodiments, the organosilicon compound comprises at least one of trimethylsilane, triethylsilane, trimethoxysilane, triethoxysilane, tetramethylsilane, tetraethylsilane, tetramethoxysilane, tetraethoxysilane, hexamethylcyclotrisiloxane, tetramethylcyclotetrasiloxane, tetraethylcyclotetrasiloxane, octamethylcyclotetrasiloxane, hexamethyldisiloxane, or bistrimethylsilylmethane. In some embodiments of the plasma treatment method disclosed herein, providing a gas inside the containers to be treated comprises providing at least one of tetramethylsilane or tetraethyoxysilane (in some embodiments, tetramethylsilane).

In some embodiments of the plasma treatment method according to the present disclosure, the gas provided to the interiors of the containers (i.e., the source gas) includes an organosilicon compound and may further comprise an additional gas or gases. Each additional gas can be added separately or in combination with each other. If a gas is mixed along with the organosilicon compound(s), the atomic percent of silicon in the gas mixture generally is calculated based on the volumetric (or molar) flow rates of the component gases in the mixture. The source gas may, for example, further comprise at least one of argon or hydrogen. Argon normally is not incorporated into the deposited coating but enhances ion bombardment, while hydrogen may promote the formation of high packing density while providing an additional source of hydrogen in the deposited composition. Optionally the source gas may further comprise at least one of ammonia or nitrogen. However, in some embodiments, the plasma-deposited diamond-like glass coating is substantially free of nitrogen (e.g. at most about 5 atomic percent of nitrogen (on a hydrogen free basis)), in some embodiments free of nitrogen. The source gas may further comprise oxygen gas. In these embodiments, the amount of oxygen gas is less than 35% on a molar basis, in particular less than 30% on a molar basis.

In some embodiments, the plasma treatment method according to the present disclosure comprises depositing an oxygen-lean diamond-like glass coating on the interior surfaces of the containers. In these embodiments, the organosilicon compound may be free of oxygen atoms, and the source gas may be free of oxygen gas. In the event the source gas comprises oxygen gas and/or an organosilicon compound including oxygen atoms, in some embodiments, the atomic ratio of oxygen (O) to silicon (Si) (O:Si) in the source gas up to 3:1, in some embodiments, up to 2.5:1, in some embodiments up to 1:1, an in some embodiments, up to 0.8:1. In some embodiments, the amount of oxygen assist gas or oxygen-containing organosilicon(s) is no more than that corresponding to 5% on an atomic basis of oxygen relative to total content of silicon on an atomic basis.

Plasma deposition of a diamond-like glass coating typically occurs at a rate ranging from about 1 to about 100 nm/second. The rate will depend on conditions including, for example, pressure, power, concentration of gas, types of gases, and relative size of the electrodes. In general, the deposition rate increases with increasing power, pressure, and concentration of gas, although the rate can approach an upper limit. In some embodiments, plasma deposition is carried out for a period of time such that the deposited diamond-like glass coating has a thickness in the range from about 5 nm to about 5000 nm. In some embodiments, the thickness of the diamond-like glass coating is at least 100 nm, 250 nm, or 550 nm. In some embodiments, the thickness of the diamond-like glass coating is up to 5000 nm, 3500 nm, 2500 nm, or up to 2000 nm.

Exemplary diamond-like glass coatings and further methods of making diamond-like glass are described in U.S. Pat. No. 6,696,157 (David et al.), the content of which is incorporated here in its entirety.

In some embodiments, the plasma treatment method according to the present disclosure includes plasma etching (i.e., plasma cleaning). In some embodiments, a plasma etching step is useful, for example, for removing a thin film layer deposited on the plasma apparatus, particularly the nozzle electrodes, in a prior step. The gas that is used to generate an etching plasma typically includes oxygen gas and a fluorocarbon (e.g., $CF_4$, $C_2F_6$, or $C_3F_8$). The molar concentration of fluorocarbon gas in the mixture is typically 0 to 60% depending upon the particular type of fluorocarbon and on the composition of the deposited layer to be cleaned. More fluorocarbon percentage is needed if the fluorine:carbon ratio of the fluorocarbon is lower or if the silicon content of the deposited layer is higher. Argon can also be a useful gas for plasma etching in combination with at least one of oxygen or a fluorocarbon. Typically for plasma etching, power densities in the range from about 0.1 to about 1 watt/square cm can be applied. Also, typically for plasma priming, flow densities of the priming gas in the range from about 0.1 to about 1 sccm/square cm can be applied. Plasma etching or cleaning can also remove oils, other organic or silicon containing residual layers, and other contaminants from the containers and from the hollow, electrically-conductive electrodes. In some embodiments of the method disclosed herein, plasma etching is integrated with plasma priming and plasma deposition. For example, plasma etching or cleaning can be used to remove a coating (e.g., diamond like glass or plasma polymer) from the nozzles and to clean the interior surface of the container. What is removed from the nozzle and container surfaces can be exhausted through the nozzles or through the physical gap surrounding the nozzles, depending on the particular embodiment of the apparatus used. Oxygen gas can then be provided inside the container under the conditions of plasma priming. In some embodiments, an oxide layer is reformed on the container interior during plasma priming. Finally, a depositing plasma can be generated, for example, using source gas containing an organosilicon compound to provide a diamond like glass coating. Advantageously, in the apparatus disclosed herein, plasma etching, plasma priming, and plasma deposition can all be carried out on at least a portion of the interior surface of multiple containers without removing the containers from the apparatus between plasma processes.

In some embodiments, the plasma treatment method according to the present disclosure comprises depositing a fluoropolymer on at least a portion of the interior surfaces of the containers. In some embodiments, pure monomer plasma is used, by which is meant that the gaseous atmosphere in which the plasma is struck and maintained consists entirely of the monomer or monomers. In some embodiments, the gaseous atmosphere includes one or more diluent gases. Exemplary useful monomers to form a fluoropolymer include $CF_4$, $C_2F_6$, $C_3F_6$, $C_4F_8$, $CF_3CHFCF_3$, $CF_3CH_2F$, $C_5F_{10}H_2$, $C_6F_{12}$, $C_6F_{14}$, and $C_8F_{18}$. These monomers may be used singly, to form a homopolymer, or as part of a blend of monomers to produce a co-polymer. Exemplary useful blends of monomers include $CF_4/C_4F_8$, $CF_4/C_2H_4$, $CF_4/CH_4$, $CF_4/C_2H_6$, $C_4F_8/CH_4$, $C_4F_8/C_2H_6$, $CF_4/CF_3CHFCF_3$ and/or $CF_3CH_2F$, $C_4F_8/CF_3CHFCF_3$ and/or $CF_3CH_2F$.

Other types of plasma polymers can be deposited using the apparatus and method according to the present disclosure. Examples of these plasma polymers include plasma polymerized organosilicons, silazanes, hydrocarbons, acrylates, glycols, and organometallics, and exemplary plasma polymers may include other functional groups from gases such as ammonia, nitrogen, sulfur dioxide, and hydrogen peroxide.

Although it was proposed in International Pat. Appl. Pub. No. WO 2008/146025 (Stevenson et al.) that a can to be plasma treated can act as an RF electrode, the configuration of electrodes, gas inlet, and exhaust outlet described in that publication would appear to result in uneven gas flow in the can and consequently provide an uneven plasma treatment within the can. The present disclosure provides an apparatus that can have an electrode coaxial with the gas inlet and exhaust pathways, thereby allowing more uniform gas flow, which would result in more uniform plasma treatment of a container in the method according to the present disclosure.

Furthermore, the present disclosure provides a remarkably effective way for plasma treating multiple containers simultaneously. The apparatus and method disclosed can be usefully scaled to a large number (e.g., greater than 1000) of containers. The apparatus according to the present disclosure is readily modifiable to achieve substantially uniform pressures among the multiple containers to be treated. In some embodiments of the apparatus and method disclosed herein, there is a pressure difference among the multiple containers of up to ten (in some embodiments, up to 9, 8, 5, 4, 3, 2, or 1) percent. The difference in pressure among multiple containers can be minimized in some embodiments by minimizing the cross-sectional area of the gas inlet and exhaust flow paths relative to the cross-sectional area of the manifold. Also, in the embodiment illustrated in FIGS. 1A, 1B, 3 and 4, the difference in pressure among multiple containers is minimized by incorporating substantially equal flow paths into and out of each container, regardless of container position.

Selected Embodiments of the Disclosure

In a first embodiment, the present disclosure provides an apparatus for plasma treating multiple containers, the apparatus comprising:

a manifold comprising a first chamber with multiple outlet openings; and multiple hollow, electrically-conductive nozzles for at least one of delivering or exhausting plasma-generating gas, wherein the multiple hollow, electrically-conductive nozzles are connected to the multiple outlet openings and protrude from the manifold.

In a second embodiment, the present disclosure provides the apparatus according to the first embodiment, wherein each of the hollow, electrically-conductive nozzles has an inner diameter in a range from 1.6 millimeters to 12.2 millimeters.

In a third embodiment, the present disclosure provides the apparatus according to the first or second embodiment, wherein each of the hollow, electrically-conductive nozzles has an inner diameter and an outer diameter, and wherein the ratio of the outer diameter to the inner diameter is in a range from 8:1 to 1.04:1.

In a fourth embodiment, the present disclosure provides the apparatus according to any one of the first to third embodiments, wherein each of the hollow, electrically-conductive nozzles has a surface dielectric coating. In some of these embodiments, each of the hollow, electrically-conductive nozzles has an anodized surface.

In a fifth embodiment, the present disclosure provides the apparatus according to any one of the first to fourth embodiments, wherein the first chamber comprises non-linear pathways between the hollow, electrically-conductive nozzles and at least one of a supply of plasma-generating gas or a vacuum source.

In a sixth embodiment, the present disclosure provides the apparatus according to any one of the first to fifth embodiments, wherein the first chamber comprises tortuous pathways between the hollow, electrically-conductive nozzles and at least one of a supply of plasma-generating gas or a vacuum source.

In a seventh embodiment, the present disclosure provides the apparatus according to any one of the first to sixth embodiments, wherein the manifold comprises a first plate having a first face and a second face, wherein the first chamber comprises a first plurality of interconnected pathways in the first face of the first plate for connecting the multiple hollow, electrically-conductive nozzles to a supply of plasma-generating gas or a vacuum source, and wherein the multiple hollow, electrically-conductive nozzles protrude from the second face of the first plate.

In an eighth embodiment, the present disclosure provides the apparatus according to the seventh embodiment, wherein the first plurality of pathways are configured such that each pathway between one of the hollow, electrically-conductive nozzles and the supply of plasma-generating gas or the vacuum source is substantially the same in volume.

In a ninth embodiment, the present disclosure provides the apparatus according to the seventh or eighth embodiment, wherein the first plurality of pathways are configured such that each pathway between one of the hollow, electrically-conductive nozzles and the supply of plasma-generating gas or the vacuum source is substantially the same in length.

In a tenth embodiment, the present disclosure provides the apparatus according to any one of the first to ninth embodiments, wherein the manifold further comprises a second chamber adjacent the first chamber, the second chamber comprising multiple passages therethrough aligned with the multiple outlet openings, wherein the multiple hollow, electrically-conductive nozzles extend through the multiple passages.

In an eleventh embodiment, the present disclosure provides the apparatus according to the tenth embodiment, wherein each of the multiple passages in the second chamber comprises a space surrounding one of the hollow, electrically-conductive nozzles.

In a twelfth embodiment, the present disclosure provides the apparatus according to the tenth or eleventh embodiments, wherein the second chamber comprises non-linear (e.g., tortuous) interconnected pathways.

In a thirteenth embodiment, the present disclosure provides the apparatus according to any one of the seventh to ninth embodiments, wherein the manifold further comprises a second chamber comprising a second plurality of interconnected pathways in a first face of an insulating block, the first face of the insulating block disposed on the second face of the first plate, wherein the first plate further comprises a port extending therethrough, wherein the second plurality of interconnected pathways is in communication with the port in the first plate and each of the second plurality of interconnected pathways extends to discrete openings in a second face of the insulating block, and wherein the multiple hollow, electrically-conductive nozzles protrude from the discrete openings in the second face.

In a fourteenth embodiment, the present disclosure provides the apparatus according to the thirteenth embodiment, wherein the second plurality of interconnected pathways is configured such that each pathway between one of the discrete openings and the port in the first plate has substantially the same volume.

In a fifteenth embodiment, the present disclosure provides the apparatus according to any one of the first to fourth embodiments, further comprising:
a second chamber having passages therethrough aligned with the multiple outlet openings in the first chamber; and
an insulating block having discrete openings extending from a first face to a second face of the insulating block and aligned with the multiple outlet openings in the first chamber,
wherein each of the hollow, electrically-conductive nozzles comprises a middle portion and two extensions on opposite ends of the middle portion, a central bore extending through the two extensions and the middle portion, and at least two outer bores substantially parallel to the central bore extending through only the middle portion, wherein the central bore taps into the first chamber, wherein the at least two outer bores tap into the second chamber, and wherein the multiple hollow, electrically-conductive nozzles protrude from the second face of the insulating block through the discrete openings.

In a sixteenth embodiment, the present disclosure provides an apparatus for plasma treatment of multiple containers, the apparatus comprising:
a manifold comprising:
a first chamber having multiple outlet openings;
a second chamber disposed adjacent the first chamber and having multiple passages therethrough aligned with the multiple outlet openings in the first chamber, wherein one of the first or second chambers is adapted to connect to a gas supply, and one of the first or second chambers is adapted to connect to a vacuum source; and
an insulating block disposed adjacent the second chamber such that the second chamber is interposed between the first chamber and a first face of the insulating block, the insulating block having discrete openings extending from the first face to a second face of the insulating block and aligned with the multiple outlet openings in the first chamber;
multiple hollow, electrically-conductive nozzles inserted through the discrete openings in the insulating block, through the multiple passages through the second chamber, and into the first chamber through the multiple outlet openings, each nozzle comprising:
a middle portion and two extensions on opposite ends of the middle portion;
a central bore extending through the two extensions and the middle portion; and
at least two outer bores substantially parallel to the central bore and extending through only the middle portion,
wherein the central bore taps into the first chamber and seals one of the multiple outlet openings, wherein the middle portion is sealed within one of the discrete openings in the insulating block, wherein the at least two outer bores tap into the second chamber, wherein the discrete opening in the second face of insulating block comprises a sealing system for receiving a container to be treated, and wherein one of the extensions protrudes from the discrete opening in the second face of the insulating block.

In a seventeenth embodiment, the present disclosure provides an apparatus for plasma treatment of multiple containers, the apparatus comprising:

multiple hollow, electrically-conductive nozzles for at least one of delivering or exhausting plasma-generating gas; and a manifold comprising:

a first chamber in a first plate, wherein the first chamber comprises a first plurality of interconnected pathways in the first plate for connecting the multiple hollow, electrically-conductive nozzles to a supply of plasma-generating gas or a vacuum source; and a second chamber comprising a second plurality of interconnected pathways in a first face of an insulating block, the first face of the insulating block disposed next to the first plate, wherein the first plate further comprises a port extending therethrough, wherein the second plurality of interconnected pathways is in communication with the port in the first plate and each of the second plurality of interconnected pathways extends to discrete openings in a second face of the insulating block, wherein the multiple hollow, electrically-conductive nozzles protrude from the discrete openings in the second face, and wherein each discrete opening in the second face of insulating block comprises a sealing system for receiving a container to be treated.

In an eighteenth embodiment, the present disclosure provides the apparatus according to any one of the thirteenth to seventeenth embodiments, further comprising a second plate comprising:

slots for multiple containers, the slots aligned with the discrete openings in the second face of the insulating block; and a connection for a radio frequency power source.

In a nineteenth embodiment, the present disclosure provides the apparatus according to the eighteenth embodiment, wherein the second plate further comprises a coolant entrance port and a coolant exit port with flow paths for coolant extending between the coolant entrance port and the coolant exit port.

In a twentieth embodiment, the present disclosure provides the apparatus according to any one of the first to nineteenth embodiments, wherein the manifold further comprises a coolant entrance port and a coolant exit port with flow paths for coolant extending between the coolant entrance port and the coolant exit port.

In a twenty-first embodiment, the present disclosure provides the apparatus according to any one of the first to ninth embodiments, further comprising:

an evacuable chamber connected to the manifold, wherein the multiple hollow, electrically-conductive nozzles extend into the evacuable chamber; and a conductive plate within the evacuable chamber in proximity to the multiple hollow, electrically-conductive nozzles, wherein the conductive plate comprises a connection for a radio frequency power source.

In a twenty-second embodiment, the present disclosure provides a method of plasma treating multiple electrically-conductive containers, the method comprising:

providing a reactor system comprising an apparatus according to any one of the first to twentieth embodiments;

inserting the multiple hollow, electrically-conductive nozzles into the multiple electrically-conductive containers;

grounding the multiple hollow, electrically-conductive nozzles while applying radio frequency power to the multiple electrically-conductive containers;

evacuating the multiple electrically-conductive containers;

providing a gas inside the multiple electrically-conductive containers; and generating a plasma to treat an interior surface of the multiple electrically-conductive containers;

wherein at least one of evacuating or providing the gas is carried out through the hollow, electrically-conductive nozzles.

In a twenty-third embodiment, the present disclosure provides the method according to the twenty-second embodiment, wherein providing the gas is carried out through the hollow, electrically-conductive nozzles.

In a twenty-fourth embodiment, the present disclosure provides the method according to the twenty-second or twenty-third embodiment, wherein the hollow, electrically-conductive nozzles are centrally disposed in (e.g., coaxial with) the electrically-conductive containers.

In a twenty-fifth embodiment, the present disclosure provides the method according to any one of the twenty-second to twenty-fourth embodiments, wherein there is a pressure difference among the multiple electrically-conductive containers of up to ten percent.

In a twenty-sixth embodiment, the present disclosure provides the method according to any one of the twenty-second to twenty-fifth embodiments, wherein each of the electrically-conductive containers has a distance between a brim and a bottom, and wherein the hollow, electrically-conductive nozzles penetrate into the electrically-conductive containers in a range from 30 percent to 99 percent of the distance.

In a twenty-seventh embodiment, the present disclosure provides the method according to any one of the twenty-second to twenty-sixth embodiments, wherein a distance between a tip of one of the multiple hollow, electrically-conductive nozzles and a bottom of one of the multiple electrically-conductive containers in a range from 1.6 mm to 38.1 mm.

In a twenty-eighth embodiment, the present disclosure provides the method according to any one of the twenty-second to twenty-seventh embodiments, wherein exhaust gas from each of the electrically-conductive containers is vented through pathways having the substantially the same volume.

In a twenty-ninth embodiment, the present disclosure provides the method according to any one of the twenty-second to twenty-eighth embodiments, further comprising controlling the temperature of at least one of the multiple hollow, electrically-conductive nozzles or the multiple electrically-conductive containers while generating the plasma.

In a thirtieth embodiment, the present disclosure provides the method according to any one of the twenty-second to twenty-ninth embodiments, further comprising depositing diamond like glass on the interior surface of the electrically-conductive containers.

In a thirty-first embodiment, the present disclosure provides the method according to any one of the twenty-second to twenty-ninth embodiments, further comprising depositing a fluoropolymer on the interior surface of the electrically-conductive containers.

In a thirty-second embodiment, the present disclosure provides the method according to any one of the twenty-second to twenty-ninth embodiments, further comprising depositing a plasma polymer on the interior surface of the electrically-conductive containers.

In a thirty-third embodiment, the present disclosure provides the method according to any one of the twenty-second to thirty-second embodiments, wherein generating a plasma comprises generating an etching plasma.

In a thirty-fourth embodiment, the present disclosure provides the method according to any one of the twenty-second to thirty-second embodiments, wherein generating a plasma comprises generating a priming plasma.

In a thirty-fifth embodiment, the present disclosure provides a method of plasma treating multiple electrically-conductive containers, the method comprising:

providing a reactor system comprising an apparatus according to the twenty-first embodiment;

inserting the multiple hollow, electrically-conductive nozzles into the multiple electrically-conductive containers;

grounding the multiple hollow, electrically-conductive nozzles while applying radio frequency power to the multiple electrically-conductive containers;

evacuating the multiple electrically-conductive containers;

providing a gas inside the conductive plate; and generating a plasma to treat an interior surface of the multiple electrically-conductive containers;

wherein at least one of evacuating or providing the gas is carried out through the hollow, electrically-conductive nozzles.

Objects and advantages of this disclosure are further illustrated by the following examples, but the particular materials and amounts thereof recited in these examples, as well as other conditions and details, should not be construed to unduly limit this disclosure.

EXAMPLES

Examples 1 and 2 were conducted to measure the pressure variability for a plurality of containers in different embodiments of the apparatus according to the present disclosure.

Example 1

An MDI canister (aluminum, 19 mL brimful capacity available from 3M Healthcare, Clitheroe UK) was modified so that it was connected to a monometer obtained from MKS Instruments, Andover, Mass., under the trade designation "BARATRON". Using an expanded and modified version of the apparatus in FIG. 8, the modified canister was inserted over one of the nozzles 10 (nozzle dimensions: 0.259 inch (6.6 mm) OD×0.237 inch (6.0 mm) ID) in a linear 1×22 manifold. The outer surface of the brim of the canister was secured to the corresponding opening in the insulating block by means of an o-ring seal. There was a physical gap surrounding the nozzle formed by the opening in the insulating block and the lower portion of the vacuum chamber. Canisters that had not been modified were similarly secured at each of the remaining 21 positions in the manifold. After the system was fully assembled, vacuum was applied and the baseline pressure was measured. Tetramethyl silane (TMS) gas was then introduced at a total flow rate of 100 sccm (nominally 4.5 sccm/can) and the pressure was measured once a steady state was obtained. The pressure difference was determined by subtracting the baseline pressure from the pressure following TMS introduction. The procedure was repeated to obtain measurements at each of the 22 canister positions in the apparatus. The average pressure difference measured at the canister positions in the apparatus was 873 mTorr (116 Pa). The maximum variability in pressure difference measured between canister positions in the apparatus was 66.4 mTorr (8.85 Pa).

Example 2

An MDI canister (aluminum, 19 mL brimful capacity available from 3M Healthcare, Clitheroe UK) was modified so that it was connected to a monometer obtained from MKS Instruments under the trade designation "BARATRON". Using the apparatus in FIG. 4, the modified canister was inserted over one of the nozzles (nozzle dimensions: 0.259 inch (6.6 mm) OD×0.237 inch (6.0 mm) ID) in the 4×4 manifold. The outer surface of the brim of the canister was secured to the corresponding opening in the insulating block by means of an o-ring seal. Canisters that had not been modified were similarly secured to each of the remaining 15 positions in the manifold. After the system was fully assembled, vacuum was applied and the baseline pressure was measured. Tetramethyl silane (TMS) gas was then introduced at a total flow rate of 100 sccm (nominally 6.3 sccm/can) and the pressure was measured once a steady state was obtained. The pressure difference was determined by subtracting the baseline pressure from the pressure following TMS introduction. The procedure was repeated to obtain measurements at each of the 16 canister positions in the apparatus. The average pressure difference measured at the canister positions in the apparatus was 844 mTorr (112.5 Pa). The maximum variability in pressure difference measured between canister positions in the apparatus was 7.9 mTorr (1.05 Pa).

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein. All patents and patent applications cited above are hereby incorporated by reference into this document in their entirety.

What is claimed is:

1. An apparatus for plasma treating multiple containers, the apparatus comprising:

a manifold comprising a first chamber and a second chamber; and multiple hollow, electrically-conductive nozzles for at least one of delivering or exhausting plasma-generating gas, wherein the manifold comprises a first plate having a first face, a second face, and a port extending therethrough, wherein the first chamber comprises:

a first plurality of interconnected grooves formed in the first face of the first plate, wherein interconnections of the first plurality of interconnected grooves are located in the first face of the first plate;

multiple outlet openings in the second face of the first plate; and multiple passages through the first plate that extend from the first face of the first plate to the second face of the first plate such that the multiple passages connect the first plurality of interconnected grooves to the multiple outlet openings;

wherein the multiple hollow, electrically-conductive nozzles are connected to the multiple outlet openings and protrude from the second face of the first plate, and wherein the first plurality of interconnected grooves provides access to a supply of plasma-generating gas or a vacuum source and provides pathways for connecting the multiple hollow, electrically-conductive nozzles to the supply of plasma-generating gas or the vacuum source, and wherein the manifold further comprises an insulating block having a first face and a second face, wherein the second chamber comprises:

a second plurality of interconnected grooves formed in the first face of the insulating block, the first face of the insulating block disposed adjacent the second face of the first plate, wherein interconnections of the second plurality of interconnected grooves are located in the first face of the insulating block, multiple second outlet openings in the second face of the insulating block; and multiple second passages through the insulating block that extend from the first face of the insulating block to the second face of the insulating block such that the multiple second passages connect the second plurality of interconnected grooves to the multiple second outlet openings, wherein the second plurality of interconnected grooves is in communication with the port in the first plate, wherein the multiple hollow, electrically-conductive nozzles protrude from the multiple second outlet openings in the second face of the insulating block, wherein if the first plurality of interconnected grooves provides access to the supply of plasma-generating gas and provides pathways for connecting the multiple hollow, electrically-conductive nozzles to the supply of plasma-generating gas, then the second plurality of interconnected grooves provides access to the vacuum source and provides pathways for connecting the multiple second passages to the vacuum source, and wherein if the first plurality of interconnected grooves provides access to the vacuum source and provides pathways for connecting the multiple hollow, electrically-conductive nozzles to the vacuum source, then the second plurality of interconnected grooves provides access to the supply of plasma-generating gas and provides pathways for connecting the multiple second passages to the supply of plasma-generating gas.

2. The apparatus according to claim 1, wherein each of the hollow, electrically-conductive nozzles has an inner diameter in a range from 1.6 millimeters to 12.2 millimeters.

3. The apparatus according to claim 1, wherein each of the hollow, electrically-conductive nozzles has a surface dielectric coating.

4. The apparatus according to claim 1, wherein the first plurality of interconnected grooves are configured such that each pathway between one of the hollow, electrically-conductive nozzles and the supply of plasma-generating gas or the vacuum source is substantially the same in volume.

5. The apparatus according to claim 1, wherein the first plurality of interconnected grooves are configured such that each pathway between one of the hollow, electrically-conductive nozzles and the supply of plasma-generating gas or the vacuum source is substantially the same in length.

6. The apparatus according to claim 1, wherein the second plurality of interconnected grooves provides access to the vacuum source and provides pathways for connecting the multiple second passages to the vacuum source.

7. The apparatus according to claim 6, further comprising a second plate comprising:

slots for multiple containers, the slots aligned with the discrete openings in the second face of the insulating block; and a connection for a radio frequency power source.

8. The apparatus according to claim 7, wherein the second plate further comprises a coolant entrance port and a coolant exit port with flow paths for coolant extending between the coolant entrance port and the coolant exit port.

9. The apparatus according to claim 1, wherein the manifold further comprises a coolant entrance port and a coolant exit port with flow paths for coolant extending between the coolant entrance port and the coolant exit port.

10. The apparatus according to claim 1, further comprising:

an evacuable chamber connected to the manifold, wherein the multiple hollow, electrically-conductive nozzles extend into the evacuable chamber; and a conductive plate within the evacuable chamber in proximity to the multiple hollow, electrically-conductive nozzles, wherein the conductive plate comprises a connection for a radio frequency power source.

11. A method of plasma treating multiple electrically-conductive containers, the method comprising:

providing a reactor system comprising an apparatus according to claim 1;

inserting the multiple hollow, electrically-conductive nozzles into the multiple electrically-conductive containers;

grounding the multiple hollow, electrically-conductive nozzles while applying radio frequency power to the multiple electrically-conductive containers;

evacuating the multiple electrically-conductive containers;

providing a gas inside the multiple electrically-conductive containers; and generating a plasma to treat an interior surface of the multiple electrically-conductive containers;

wherein at least one of evacuating or providing the gas is carried out through the hollow, electrically-conductive nozzles.

12. The method according to claim 11, wherein the hollow, electrically-conductive nozzles are centrally disposed in the electrically-conductive containers.

13. The method according to claim 11, wherein there is a pressure difference among the multiple electrically-conductive containers of up to ten percent.

14. The method according to claim 11, wherein each of the electrically-conductive containers has a distance between a brim and a bottom, and wherein the hollow, electrically-conductive nozzles penetrate into the electrically-conductive containers in a range from 30 percent to 99 percent of the distance.

15. The method according to claim 11, wherein exhaust gas from each of the electrically-conductive containers is vented through pathways having substantially the same volume.

16. The method according to claim 11, further comprising controlling the temperature of at least one of the multiple hollow, electrically-conductive nozzles or the multiple electrically-conductive containers while generating the plasma.

17. The method according to claim 11, further comprising depositing diamond like glass on the interior surface of the electrically-conductive containers.

18. The method of claim 11, wherein at least 8 and up to 2500 of the multiple electrically-conductive containers are arranged in rows in a two-dimensional array.

19. The apparatus according to claim 6, wherein the second plurality of interconnected grooves is configured such that each of the second plurality of interconnected pathways between one of the discrete openings and the port in the first plate has substantially the same volume.

* * * * *